United States Patent
Mottin

(10) Patent No.: US 7,265,826 B2
(45) Date of Patent: Sep. 4, 2007

(54) METHOD AND DEVICE FOR THE DIFFERENTIAL SPECTROPHOTOMETRY OF NON-CLEAR MEDIA BY MEANS OF SPECTRO-TEMPORAL IMAGING IN COUNTING MODE

(75) Inventor: Stephane Mottin, Saint Genest Lerpt (FR)

(73) Assignees: Centre National de la Recherche Scientifique, Paris (FR); Universite Jean Monnet, Saint Etienne (FR)

( * ) Notice: Subject to any disclaimer, the term of this patent is extended or adjusted under 35 U.S.C. 154(b) by 406 days.

(21) Appl. No.: 10/522,726

(22) PCT Filed: Jul. 30, 2003

(86) PCT No.: PCT/FR03/02411

§ 371 (c)(1),
(2), (4) Date: Jan. 28, 2005

(87) PCT Pub. No.: WO2004/013617

PCT Pub. Date: Feb. 12, 2004

(65) Prior Publication Data

US 2006/0092422 A1 May 4, 2006

(51) Int. Cl.
*G01J 3/28* (2006.01)
*G01N 21/49* (2006.01)

(52) U.S. Cl. .................... 356/319; 356/328

(58) Field of Classification Search ............. 356/319, 356/326, 328
See application file for complete search history.

(56) References Cited

U.S. PATENT DOCUMENTS 5,692,504 A 12/1997 Essenpreis et al.

FOREIGN PATENT DOCUMENTS

| EP | 0 526 134 | 2/1993 |
| WO | 01/22063 | 3/2001 |

OTHER PUBLICATIONS

Leonardi, Lorenzo et al. "Quantitative Multiwavelength Constituent Measurements Using Single-Wavelength Photon Time-of-Flight Correction", Applied Spectroscopy, vol. 53, No. 6, pp. 637-646, XP000827482 1999.

Andersson-Engels, S. et al. "Multispectral tissue characterization with time-resolved detection of diffusely scattered white light", Optics Letters, vol. 18, No. 20, pp. 1697-1699, XP001090866 1993.

Gleckler, Anthony D. "Multiple-Slit Streak Tube Imaging Lidar (MS-STIL) Applications", Proceedings of the SPIE, vol. 4035, pp. 266-278, XP008001327 2000.

(Continued)

*Primary Examiner*—F. L. Evans
(74) *Attorney, Agent, or Firm*—Oblon, Spivak, McClelland, Maier & Neustadt, P.C.

(57) ABSTRACT

According to the invention, to analyse a non-limpid medium, this medium is lit by at least one light pulse, a spectral and temporal transmission image, in counting mode, is acquired from the lit medium, and the image and derivatives thereof are processed so as to acquire information about the non-limpid medium. The invention applies to the analysis of diffusing and absorbing media, for example milk.

15 Claims, 2 Drawing Sheets

OTHER PUBLICATIONS

Figure 1:
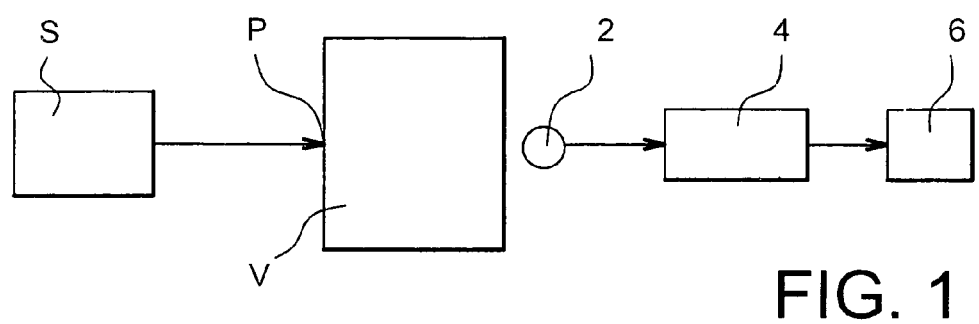

Watanabe, M. et al, "Development of a new fluorescence decay measurement system using two-dimensional single-photon counting", J. Photochem. Photobiol. A: Chem, vol. 80, pp. 429-432.

Glasser, M.L. et al. "Extended Watson Integrals for the cubic lattices", Proc. Natl. Acad. Sci., vol. 74, No. 5, pp. 1800-1801 1977.

Kienle, Alwin et al. "Improved solutions of the steady-state and the time-resolved diffusion equations for reflectance from a semi-infinite turbid medium", J. Opt. Soc. Am. A, vol. 14, No. 1, pp. 246-254 1997.

Bakhvalov, N. et al. "Homogenisation: Averaging Processes in Periodic Media", vol. 36, pp. ii-xi 1989.

Du, Hai et al, "PhotochemCAD: A Computer-Aided Design and Research Tool in Photochemistry", Photochemistry and Photobiology, vol. 68, No. 2, pp. 141-142 1998.

Mottin, Stephane et al. "Fiber-Optic Time-Resolved Fluorescence Sensor for in Vitro Serotonin Determination", Applied Spectroscopy, vol. 47, No. 5, pp. 590-597 1993.

Sandorfy, C. et al. "Les Spectres Electroniques En Chimie Theorique", Revue d'optique theorique et Instrumentale, pp. 40, 41, 228-230 1959.

Ishimaru, Akira. "Wave Propagation and Scattering Random Media: Single Scattering and Transport Theory", vol. 1 1978.

Ishimaru, Akira. "Wave Propagation and Scattering in Random Media: Multiple Scattering, Turbulence, Rough Surfaces, and Remote Sensing", vol. 2 1978.

Mottin, Stephane et al. "Systemes femtosecondes pour l'etude des milieux heterogenes compartimentes absorbants et diffusants", Publications de l'Universite de Saint-Etienne, pp. 405-408 2001.

METHOD AND DEVICE FOR THE DIFFERENTIAL SPECTROPHOTOMETRY OF NON-CLEAR MEDIA BY MEANS OF SPECTRO-TEMPORAL IMAGING IN COUNTING MODE

TECHNICAL FIELD

This invention relates to a pulse spectrophotometry process and device.

The invention applies to the analysis of media that are not limpid and has applications in various fields, in particular:
  the analysis of milk and dairy products,
  the control of products such as meat, eggs, fruit and fish,
  the control of slurries,
  the control of industrial waste,
  the medical field, and
  the analysis of granular, porous or fractured media.

STATE OF THE PRIOR ART

Various techniques of spectrophotometry of limpid media are already known.

In particular, spectrophotometry techniques of limpid media are known which permit the measurement of the absorption on an entire spectrum, without scanning, in particular using detectors comprising photo diode strips.

These techniques make possible differential spectrophotometry and the analysis of colorant mixtures in real time, in the case of such limpid media and even in the case of very slightly diffusing media.

Let us point out that this invention allows the first, second and nth partial derivatives of the photonic flows measured with respect to the wavelength and time to be determined, in addition to the information that these known techniques permit to obtain.

Various time resolved spectroscopy techniques are also known: for time resolved fluorescence, fluorescence spectro-temporal imaging has already been proposed.

Such imaging provides access to spectral and temporal distributions, that are specific to the fluorescence decay time analyses of several constituents.

It should however be noted that the interest of differential pulse spectrophotometry for the spectro-temporal imaging of transmittance, with a wide spectrum pulsed light source, is neither divulged nor suggested in the prior art (such as the document WO 01/22063 A1). Only spectral and temporal resolutions had been explained but never has the use of partial derivations in function of the flying time and/or of the spectrum been envisaged in view to a chemical and physical analysis of non-limpid media.

Moreover, it should be noted that in the scope of spectro-temporal imaging of the transmittance of non-limpid media, the single photoelectrons or SPE counting mode is as powerful as for the spectro-temporal imaging of fluorescence, as it permits the photonic flows to be measured not as an arbitrary unit but as a counting event unit. This also makes possible more dynamic measurement.

The counting mode is achieved by binarisation of the image by thresholding. This binarisation causes the detection chain noise to be reduced to zero. This non-linear thresholding operation permits the use of an integration window over a very long time (that may exceed several hours). This mode permits rare events to be counted linked to the non-absorbed photons having spent a long time in the study medium. These "escaped" photons contain a great deal of information on the volume tested. The detection of a pixel zone that can be attributed to this photoelectron is carried out by thresholding and adequate processing. The counting mode incorporates the reduction of this zone (in the form of a disc or specific geometry) to a single pixel or to coordinates at a sub-pixel scale.

We can also refer to the following document:

S. Anderson Engels et al., ("Multispectral tissue characterisation with time resolved detection of diffusely scattered white light" Optics Letters (1993), 18, pp. 1697-1699.

However, this document has been used very little and remains limited to the field of tissue optics, without any mention of an application to analytic chemistry nor aspects of probability or statistics of this type of imaging (such as SPE counting and the use of partial derivatives).

As concerns the counting, we may also refer to the following document and patents registered by Hamamatsu at the beginning of the Nineties:

Watanabe M., Koishi M., Fujiwara M., Takeshita T. and Cieslik W. (1994), Development of a new fluorescence decay measurement system using two dimensional single photon counting, J. Photochem. Photobiol. A. Chem. 80, 429-432.

However, this document is directed towards two dimensional single photon counting on light emission by fluorescence or any other emission at a different wavelength from the initial source but never in transmittance and in particular in transmittance of a pulsed white laser.

PRESENTATION OF THE INVENTION

This invention proposes a process and device for the analysis of a non-limpid medium.

In particular, the invention aims to measure globally and in situ the concentrations, or variations of concentrations, of absorbers and diffusers in a non-limpid medium.

More precisely, the purpose of this invention is a differential spectrophotometry process for analysing a non-limpid medium, this process being characterised in that:
  the non-limpid medium is lit by at least one light pulse permitting the subsequent use of the partial derivative according to the wavelength, of at least one spectro-temporal transmission image acquired from the medium thus lit,
  via at least one light collector and from the medium thus lit, at least one spectro-temporal transmission image is acquired in counting mode, permitting the subsequent use of the partial derivatives of the image according to the wavelength and the flying time of the light pulse, and
  the image and its partial derivatives are processed according to the wavelength and the flying time to acquire the information on the non-limpid medium.

According to one preferred embodiment of the process that is the subject of the invention, the hyper-diffusive photons not absorbed by the medium over a wide spectral range are used, in the aim of detecting a singularity of the absorption and/or diffusion, permitting the use of derived operators, these hyper diffusive or escaped photons being emitted by the medium when it is lit.

In preference, the flying time of the light source and the spectral data will be used conjointly to establish an identity portrait of the non-limpid medium and the associated partial derivatives.

The wise use of the statistical nature of this identity portrait permits the scales and modes of homogenisation of the media tested to be qualified with respect to the contents of absorbers and diffusers.

The non-limpid medium may be lit by a single wide spectrum light pulse.

According to one particular embodiment of the process that is the subject of the invention, the partial derivatives linked to the variations of flying times and spectrum of the diffusive and ergodic photons not absorbed by the medium over a wide spectral range are used, in the aim of qualifying the degree of homogenisation of the medium tested or to detect a singularity of absorption and/or diffusion, these diffusive and ergodic photons being emitted by the medium when it is lit.

The partial derivatives linked to the flying time of the light pulse and the spectral data may be used conjointly to establish a spectro-temporal identity portrait of the non-limpid medium.

The collector may be lit without testing the medium and at the same time the non-limpid medium by one or more light pulses permitting spectro-temporal imaging that may be derived with respect to the wavelength and time, with two peaks simulating a double beam.

This invention also relates to a differential spectrophotometry device, for analysing a non-limpid medium, this device being characterised in that it comprises:
- a pulse light source to light the non-limpid medium and which allows the subsequent use of the partial derivative, according to the wavelength, of a spectral and temporal transmission image acquired from a medium thus lit,
- means for acquiring, from a medium thus lit, a spectral and temporal transmission image, with or without spectral scanning, in counting mode, and with a wavelength pitch and a time pitch permitting the subsequent use of the partial derivatives of the image according to the wavelength and the flying time of the light pulse, and
- means for processing this image, considered as the zero order moment, and its partial derivatives according to the wavelength and time, to acquire information on this medium.

According to a first particular embodiment of the device that is the subject of this invention, the pulsed light source comprises non linear means for generating femtosecond or picosecond or nanosecond light pulses permitting the use of the partial derivative according to the wavelength.

According to a second particular embodiment of the device that is the subject of this invention, the pulsed light source comprises femtosecond or picosecond or nanosecond continuum means for generating and amplifying a continuum, the continuum permitting (without scanning) the direct use of the partial derivative according to the wavelength.

The acquisition means may comprise a streak camera in counting mode or a streak camera for counting photoelectrons only, in single shot mode or in synchro-scan mode or in analogue mode.

A spectrophotometry process which complies with the process that is the subject of this invention is also proposed, that allows a true optical identity portrait of the volume tested to be established, which is to say a true signature of the statistical nature of the medium with respect to the more or less homogeneous contents of the diffusers and absorbers, this optical identity portrait being in the form of several spectro-temporal images allowing simultaneous access to the temporal distributions for a given spectral window, to the spectral distributors for a given time interval, to the partial derivatives of these two distributors as well as to their integrals.

A spectrophotometry and tomography process is also proposed that complies with the process that is the subject of the invention, in which the partial derivatives are used conjointly, with respect to the wavelength, the flying time and space, of the spectro-temporal images and mono-point modes with spatial scanning or commuted multi-point modes of the injection zones and/or the light collection zones, the use of these space type partial derivatives being then possible and permitting certain cases on non-constant densities in the volume tested to be processed, this tomography process with spectro-temporal image differentials permitting, on the one hand, the identification of a singularity of the concentration of absorbers and/or diffusers and, on the other hand, a molecular identification of these absorbers, the injections and collections of the light being able to be carried out either at the surface or within the volume.

A differential spectrophotometry process is also proposed that complies with the process that is the subject of the invention, in which the partial derivatives are used conjointly, with respect to the wavelength and time, of the spectro-temporal transmittance imaging and counting modes by binarisation of the image and then detection of a pixel zone that can be attributed to a photoelectron and reduction of this zone to a single lit pixel, or at a sub-pixel scale, in order to increase the dynamics and qualify the single photoelectron measurement.

According to one particular embodiment that is the subject of the invention, the partial derivatives in time and wavelength of the temporal queue linked to the ergodic photons diffused by the medium when it is lit are used, with the aim of measuring very low variations of an absorber.

It is possible to use, with a view to measure or homogenise the contents in absorbers and/or diffusers, spectro-temporal imaging and the operators $\partial/\partial t$, $\partial^2/\partial t^2$, $\partial/\partial \lambda$, $\partial^2/\partial \lambda^2$, $\partial^2/\partial t \partial \lambda$ up to the higher orders, these operators applying to the spectro-temporal imaging.

In this way, the spectro-temporal imaging used in this invention makes possible access to operators of the type $\partial^n/\partial t^m \partial \lambda^{n-m}$ where m<n.

In this invention, it is possible to use conjointly the fluctuations of the spectro-temporal transmittance images and the associated operators (for the fluctuations over a macroscopic time for example at a second scale, the operator $\partial/\partial e^{macroscopic}$ and the nth derivatives) in order to carry out dynamic measurements of opacimetry, colorimetry and granulometry.

BRIEF DESCRIPTION OF THE DIAGRAMS

Figure 2:
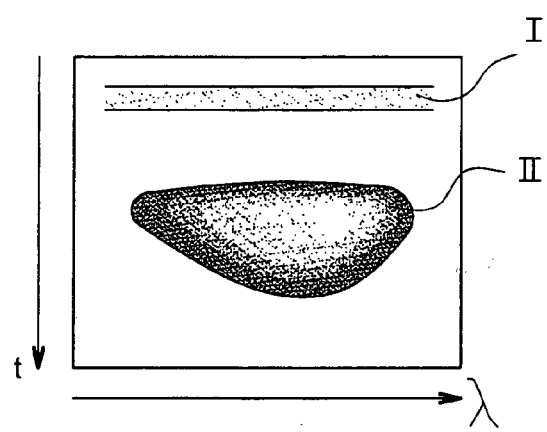
Figure 3:
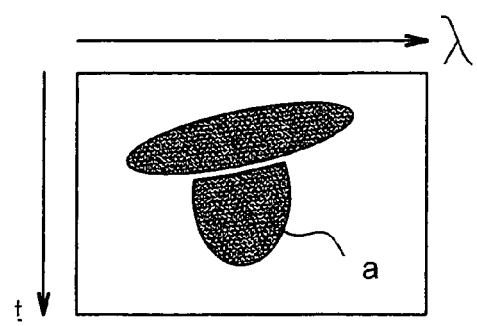
Figure 4:
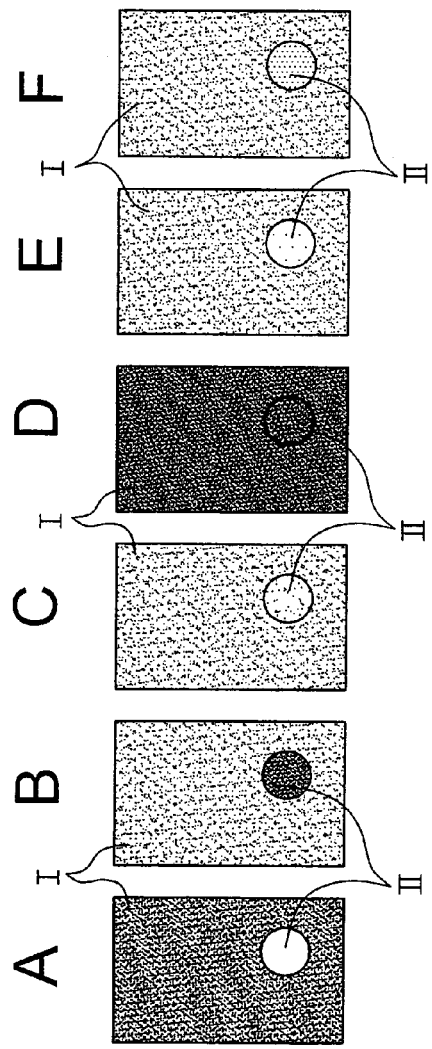
Figure 5:
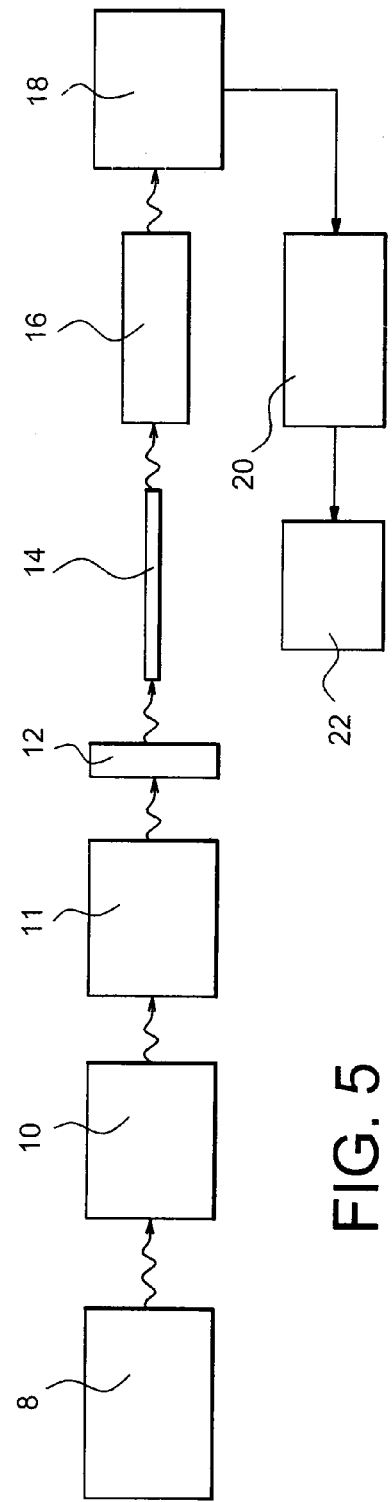

This invention will be easier to understand upon reading the description of the examples of embodiments provided hereunder, purely by way of illustration and in no way restrictively, by referring to the appended diagrams, in which:

FIG. 1 is a schematic view of a device in accordance with the invention,

FIG. 2 illustrates schematically the spectro-temporal transmission image by recording the white pulse before the media to be tested and at the same time the pulse transmitted by these media with the device of FIG. 1, FIG. 3 illustrates schematically the spectro-temporal transmission image provided by the display means comprised in the device of FIG. 1, FIG. 4 illustrates schematically examples of the statistical nature of two phase media that can be studied with the invention, FIG. 5 is a schematic view of an example of a device of the invention.

DETAILED PRESENTATION OF PARTICULAR EMBODIMENTS

We will first explain the general principle of the invention which relates in particular to the exploration of "ergodic" or "escaped" photons for chemical analysis.

In a limpid medium, passing from the measurement of an optical transmittance at a concentration (or at several concentrations of various colorants) is obtained by the classic Beer Lambert law, which is widely used in spectrophotometry.

The invention consists in particular of extending this approach to non transparent media, for example industrial slurries, media containing suspensions, milk, cheese, meat, biological tissues, and more generally turbid media, which is to say diffusing and absorbing media.

The invention may be considered as a generalisation of classic continuous spectrophotometry; it may be presented as a colorimetry and opacimetry technique for complex media.

It also permits the degree of homogeneity of a medium tested to be qualified and to discern when the grandeurs of mean concentration of absorbers and/or diffusers are meaningful for the volume in question (the volume considered of the medium).

With the use of partial derivatives, the invention uses in particular the non absorbed hyper diffusive photons over a wide spectral range, ranging from ultraviolet to infrared, and over a wide range of flying times, to detect a singularity of absorption and/or diffusion in a volume composed of materials that for example are granular, fractured or porous.

The rare counting events of such photons, composing the ergodic photons, bear important information on the mean volumic value whose statistical meaning may be compared in particular with the survival rates. It should be noted that the absorption properties are measured by the non absorbed and therefore surviving photons.

The partial derivatives with respect to the wavelength permit the characters of different monotonies between absorption and diffusion to be separated. The partial derivatives with respect to the flying times determine objective and sensitive criteria on the nature of the coupling between the diffusive modes linked to the macroscopic and mesoscopic organisation of the medium and on the molecular absorptions. The crossed partial derivatives permit the doubts on the conjunction between the various propagations and absorptions to be removed.

At the end of this description, an example is provided of a method of using the partial derivatives of the spectro-temporal image.

If the diffusion modes remain constant, the invention permits very slight absorption variations to be detected and the probability of absorption corresponding to the photons considered. For a constant distribution of absorbers (if the medium is a multiple scale isotropic, and for a same mean density), the invention permits slight diffusion variations to be detected.

From a technical point of view, the invention is based on obtaining and analysing spectro-temporal transmission imaging without spectral scanning in view to use partial derivative type operators. This differential spectro-temporal type imaging is obtained by coupling a wide spectrum pulsed light source, ranging from ultraviolet to infrared, with a streak camera in counting mode or analogue mode.

The pulse response of a volume of interest provides access to the optical transfer function in the form of an image in an identifier whose first axis is a spectral window and whose second axis is a time window that corresponds to a temporal deflection.

The joint use of the flying time of the light and spectral data and their derivatives permit a true "optical identity portrait" to be established for the volume tested, which is to say a true signature of the statistical nature of the medium with respect to the more or less homogenous contents of the diffusers and absorbers.

In an image form, assimilating roughly the photons to walkers, and in order to underline the importance of the statistical aspects, the optical process may be considered as follows:

At a given moment, thousands of walkers leave a stadium in a very short time. Each walker has a shirt that can range from red to blue depending on the size, the blue being the bigger ones. Each walker advances at a mean speed of around 0.214 mm/ps. The blues are slightly slower than the reds on average.

The counting device is a certain known distance from the stadium. Between this observation point and the stadium, are located the media to be studied, which, in a very picturesque way and virtually in two dimensions, may be a complex city.

The observer counts the number of walkers according to their colours and accumulates the counts for a time window for example every 2 ps over a time interval of for example 960 ps (2 ps/pixel*480 pixels). This series of 480 points is directly used to estimate the partial derivatives approximately according to the transport time.

Some of these walkers leave the stadium directly at the position where the counting device is positioned. These are the winding or ballistic photons. They have been extensively studied and have been the subject of many patents as they permit, in particular, projection imaging such as in X rays. The "ergodic" photons are the photons that have the longest contact times with the media to be studied. Between these two extreme cases, many transport modes are possible. The partial derivatives also diagnose the nature of these modes. It is not only the temporal distribution but above all the variations of temporal distribution of these walkers between the winding and ergodic that provide information on the statistical nature of the exploration of the media. The variations of the spectral distribution of these walkers provide information especially on the "dead" nature by absorption of these walkers. Finally, it is by saving the two distributions simultaneously and by determining the their partial derivatives that the identity portrait of the media tested are obtained.

In limpid media, between the stadium and place of counting, the problem of the volume tested may be reduced to a length, hence a working space whose dimension is equal to 1.

In non-limpid and not necessarily homogenisable media, the problem remains the volumic nature and its pseudo-fractal nature (which is to say the dimension of the work space) is between 1 and 4 and is an unknown.

The imaged example of the city is in fact a case where the dimension of the work space is of between 1 and 3 if the transport places are all on a same surface.

For the dimensions 1 and 2 and in the simple case of a lattice, the mathematician G. Polya showed in 1921 that the probability of the random walker coming back to his starting point is equal to 1 (after an infinite length of time). Here, all of the points of a lattice are without any absorption. For the dimensions greater than 2, this is no longer the case. The famous constants of Polya (see Glasser M, L and Zucker I. J. "Extended Watson Integrals for the Cubic Lattices" proc. Nat. Acad. Sci. USA 74, 1800-1801, 1977). For the dimensions 3 and 4, the probabilities respectively represent 0.340537 and 0.1932.

In this way, even with a same simple diffusion mode (random walker) on a dimension 3 lattice and even with a very high integration time, the ergodic photons cannot test the volume totally. If the medium approaches dimension 2, the ergodic photons may approach an almost complete test for a very slightly absorbing medium. Unfortunately, the structuring modes of the diffusers and absorbers are far from these simple cases. The use of differential spectrophotometry in wavelength and flying time, with movements of the light sources and/or the detection points should allow all of the real cases to be dealt with, which are far from a simple whole dimension lattice.

A device corresponding to the preceding description is illustrated schematically in FIG. 1 where a volume concerned V can be seen, a pulse light source emitted by this source onto the volume v, means 2 for detecting the light that has passed through the volume V, electronic means 4 for processing the signals provided by the means 2 that are also called a collector (and that may be, for example, an optical fibre, a lens or a micro-camera) and display means 6 with which the means 4 are equipped.

FIG. 2 illustrates schematically the spectro-temporal transmission image by recording the white pulse before the media to be tested and at the same time the pulse transmitted by these media.

We can see the instrumental function (for the image of the walkers, the convolution of leaving the stadium and the detection without passing via the city, in the air for example) before the medium (I) and after the medium (II). The x axis shows the wavelength λ of the light (in nanometres) and the y axis the time t (typically in picoseconds per pixel).

The device and the process that are the subject of this invention permit the instrumental function and the optical response to be recorded via the media tested. This recording is then carried out at the same time, simulating a double beam by an adapted temporal doorway, sufficiently distant to avoid a pile up.

FIG. 3 illustrates schematically the spectro-temporal transmission image provided by the display means 6, with the recording of simply the instrumental function or simply the optical response through the media tested. The wavelength λ (in nanometres) is shown on the x axis and the time t (typically in picoseconds per pixel) on the y axis. It is pointed out that the image a corresponds, in the example shown, to the counting of the photo-electrons in analogue mode.

Which is to say $I_o$ the intensity of the incident light that will pass through the volume V, according to the classic Beer Lambert notation used in spectrophotometry for limpid media. In this non pulsed spectrophotometry, it is very common to have devise with two beams, one passing via the coloured tank and the other permitting this $I_o$ to be measured.

The invention also permits "two shot" spectro-temporal imaging to be carried out by means of its pulsed nature: $I_o$ or the instrumental function is measured, which is to say the convolution of leaving the stadium and the detection without the media to be studied, with respect to the analyses of the flying time of the photons. It is pointed out that the measurement of $I_o$ may be carried out by means of a light leak, before the propagation in the volume V or sequentially.

It is pointed out that in a mode less than 1000 femtoseconds, the energy sent is contained in a pulse of equivalent length of less than 0.3 mm in a vacuum. However if the object to be analysed has grandeurs that are characteristic of around 100 metres, nanosecond pulses may be used as those which are supplied by hydrogen flash lamps, and deflection times of around a hundred nanoseconds.

However, for reasons of absorption probability and above all for counting level, the invention is especially useful to test volumes of less than around ten m$^3$ to volumes of around a mm$^3$.

The lower limit of the volume that can be tested only depends on the performances of the deflection system of the streak camera, to which we will return later, as wide spectrum sources (and which correspond to ultra-short sources of a few fs) are already known.

We will now describe an example of the process which is the subject of the invention.

We begin by injecting, either on the surface or in the volume to be measured, an ultra short pulse, with a very wide spectrum in the window composed by the ultraviolet, visible and near infrared fields. The most well known examples of this type of pulse are ultra short femtosecond pulses with a wide spectrum at the oscillator output, the pulses resulting from the generation of a femtosecond or picosecond continuum and/or the amplification of a continuum.

The injection and the collection of the light may be carried out either in single point mode or in multi-point mode with or without automatic displacement.

The use of a spectro-temporal image pile with this type of displacement permits optical tomography, which is to say (1) identification of the singularity of the concentration of absorbers and (2) molecular identification of these absorbers.

The collection may be carried out either at the surface or within the volume.

The light collected is analysed by a diffracting element (prism or grating spectrograph or other optical diffraction device), permitting the use of the derivative according to the wavelength and coupled to a streak camera or any device permitting temporal deflection of the light of a spectral window authorising the use of the derivative according to the flying time.

We thus obtain a spectro-temporal image of the temporally deflected "rainbow", which may be derived. Different mathematic analysis modes may be used to resolve the inverse problems which aim at quantifying the grandeurs of the medium traversed that may be homogenised.

Essential aspects of the invention are the use of this image and its partial derivatives as means both qualifying and quantifying all of the optical properties of an object and the arrival at various degrees of formation of volumic means or the decision not to form a volumic means.

It should be remembered that for a given wavelength, generally three types of photons are defined according to the temporal distribution:

a) the ballistic photons which are the first to arrive and have not undergone a diffusion event, b) the winding photons which arrive just after the ballistic photons and can still be used for imaging purposes in turbid media, and which in spite of several diffusion events maintain information of their initial direction, and c) the diffusive photons which arrive well after the previous ones.

In this invention, we also consider a fourth class, which is to say the class of hyper diffusive or ergodic photons. In spite of their long contact time with the medium (or long flying time), those which are measured have been non absorbed as the first three classes.

Outside of these 3 or 4 classes, the invention concentrates on the partial derivatives according to the wavelength and flying time and on the counting mode.

The measurement of this class of hyper diffusive single photoelectrons (SPE) corresponds to very rare elements. These photons contain considerable and often decisive information. Unfortunately, their importance must be put into perspective due to their low counting rate that allows the counting modes to be compensated.

Furthermore, following the image of the walker, it remains difficult to determine if these ergodic photons have tested the entire volume concerned or if they have remained trapped in a hyper-diffusing singularity (a case very different from the ideal lattice of Polya). On the other hand, if the medium is similar to the isotropic lattice with an isoprobability, the slightest fluctuation of the content of the absorbers is often fatal.

However, overall, the spectral distribution, the variations of this distribution (first derivative) and the nth derivatives and the crossed derivatives of all of the photons and more especially the hyper-diffusing photons permit this type of ambiguity to be cleared. The dynamics of the measurement are therefore crucial. The switch to SPE increases the dynamics considerably. Apart from the wavelength and temporal deflection axes, the z axis in SPE units is very important. The spectro-temporal imaging in counting mode has a very large potential as it reaches the limits of these optical techniques with respect to the dynamics of the measurement to count and accumulate these ergodic photons.

The image of the walkers is dangerous. In fact, the propagation of the light in a dense medium is considered as a disturbance in an electrically induced field and a magnetically induced field, both oscillating with a period of 1 to 3 femtoseconds (for example for the 300-900 nm window). The propagation of the light is therefore carried out by dipoles, of molecular size, which re-induce an electromagnetic field in a cushioned way. The dense medium structure with supra-molecular scales induces various diffusion/diffraction systems (Rayleigh, Mike, Fraunhofer).

In a limpid medium, diffusion phenomena occur but only cause a variation of direction (refraction law). The standard deviation of this direction depends on local fluctuations of the density and cushioning of the dipoles, which is to say the distribution of the refraction index n which may often be estimated by a Dirac distribution. For example, for a fixed homogenous temperature and for a given wavelength, n is equal to 1.4.

We can consider all diffusing media as a non-periodic polyphasic medium where various scales more or less close to the wavelength intervene. In this type of medium, the secondary waves, which is to say replaced by the oscillating dipoles, no longer constructively interfere to favour a direction.

In contrary to the virtually direct waves (often called ballistic or winding photons), diffusive waves have been paid much less attention. The case of "ergodic" photons means that they may be considered as residual waves with a very strong phase offset or a huge lag. These ergodic photons measured have consequently been re-emitted by numerous oscillating non absorbing dipoles.

These hyper-diffusing photons have often been considered as those containing the least information.

Whilst it is true that they may be considered as poor in terms of imaging techniques and geometrical optics, they are nevertheless rich in information of volumic mean in the sense of the walkers or also in the sense of electromagnetic waves. For example, these hyper-diffusive waves are by far the most sensitive to the slightest absorbent singularity and more globally to the imaginary part of the refractions indices.

The author of this invention has found that these hyper-diffusive photons are likely to form an excellent means to test a complex volume and carry a lot of information on this explored volume, but that degrees of extra freedom are required to decouple the absorption and the various systems of induction/diffusion permitted y differential spectrometry in spectrum and in flying time. The counting mode also highlights this analysis.

The pertinence of the wide spectrum pulse response, not just with a few discrete wavelengths, is partially based on the fact that:

the diffusions are most often monotone according to the wavelength, and the absorptions are most often non monotone (presence of peaks and troughs), as is well known in differential spectrophotometry and optical chemometry.

In the classes of the temporal distribution of measured photo-electrons, those which contain the most information with respect to the volume tested are the last classes, which is to say those with the longest times.

Furthermore, the probability of non absorption after a "journey" of L mm varies as exp (−L/La) where La (in mm) is the absorption length, expressed by the Beer Lambert law. The grater the journey, the greater the probability of non absorption diminishes exponentially. In the case of the imaging proposed in this invention, we can also speak of logarithmic imaging. The differential spectrophotometry permits wise use of this logarithmic character.

Moreover, the switch from "interaction time" to "interaction length" leads to the writing of the mean speed.

The geometrical problem is in fact more complicated. Thus, it is not easy to separate a hyper-diffusive photon which has spent a long time in a small volume by hyper-testing the latter, from that which has tested a larger volume and which has not passed twice on the same site (called a self-excluding journey). It can simply be affirmed that the entry and exit points are known and the interaction time.

Backtracking along an interaction journey requires hypotheses or knowledge of the structuring of the medium.

It is pointed out that the invention is not limited to the joint use of the transmission spectrum and the distribution of the flying time and their partial derivatives. It also concerns the use of a displacement of the impact and/or collection points in order to carry out a tomography (using the space type partial derivatives). With these degrees of extra freedom, the spectral and temporal distributions allow the contents of absorbers and/or diffusers to be better qualified and situated in a volume of singularities.

More generally, the spectro-temporal imaging allows the access to the $\partial^2/\partial t \partial \lambda$ operator and to the higher orders, with the sampling comb function (for example 480 pixels for 1.1 ns and 640 pixels for 180 nm, given that this can change depending on the polychromater and the camera used at the end of the acquisition chain).

In traditional differential spectrophotometry, access is only available to the $d^n/d\lambda^n$ operators and, with flying time techniques of just a few discrete wavelengths, to the $\partial^n/\partial C_i^n$ operators, where Ci is the concentration of the $I^{th}$ absorber, and the crossed operators of the $\partial^n/\partial C_i \partial \lambda$ type. The imaging proposed in this invention permits access to new operators.

Various mathematical analysis modes can be used to resolve the inverse problems that aim at quantifying the grandeurs of the medium traversed that may be homogenised.

We can consult the following document: Kienle A., Patterson M. S., (1997), Improved solutions of the steady state and the time resolved equations for reflectance from a semi-infinite medium, J. Opt. Soc. Am. A 14 246 254.

for a semi-infinite geometry, for a work space whose dimension is placed equal to 3, for an infinitely short impact point of an infinitely small diameter on the surface, for a collection point on the surface quite distant from the point of impact, and for a quite homogeneous medium, where the estimation of the diffusion of the light is valid and where the contents of the absorbers and the diffusers can be homogenised and reduced to two parameters ($u_4$ in mm$^{-1}$ and $u_8$ in mm$^{-1}$).

At the end of this description, we will provide several examples of processing and the advantages of new operators.

Many mathematical approaches have been proposed in the prior art to resolve the inverse problem of turbid media, both from the point of view of measurement of the concentration means of absorbers and diffusers as from the point of view of the geometry mean of the diffusers (granulometry).

The spectro-temporal imaging as it is described permits simultaneous access to the temporal and spectral distributions and to their partial derivatives, as well as to their integrals. These means permit the statistical nature of the media traversed to be qualified (optically "meanable" or not). If geometrical knowledge or various local contents of absorbers or diffusers are added, the mathematical problem is simplified and may allow, according to the case, to measure the contents of absorbers or diffusers more precisely.

Regardless of the choices of the methods of mathematical analysis (methods such as Monte Carlo, radiative equations, or Maxwell equations for example), the spectro-temporal imaging proposed in this invention procures an optical and empirical identity portrait of the media tested. The statistical study of its variations by means of the partial derivatives permits the variabilities of the media explored to be qualified directly.

Furthermore, the use of hyper-diffusive photons allows the switch from spectro-temporal imaging to quantified information on the subject of the volume studied. These formations are either of a geometrical nature (tomography, detection of singularity) or a chemical nature (chemometry, quantification of concentration).

The invention is thus situated at two levels:

1) establishing the optical identity portrait (spectro-temporal images and their partial derivatives in wavelength and flying time): this is limited to a quality control;

2) use of the optical identity portrait: we try to analyse the journey of the hyper-diffusive photons to homogenise the contents in absorbers and/or diffusers or decide to establish a mean.

If the homogenisation is valid, the concentration in absorbers and diffusers has a sense and can be quantified.

Let us return in more detail to one of the problems that this invention resolves.

We wish to make a global measurement and in situ of the variations in concentrations of absorbers and diffusers in a on limpid medium. Furthermore, the invention aims at determining when it is valid to speak of mean concentration and permit testing of the homogenisation hypothesis.

Let us briefly illustrate certain classes of problems. We may wish:

to measure a concentration of colorant in a turbid medium, for example endogenous flavins in milk, or to measure colorants in a suspension, to measure the concentrations of various colorants, for example a blue colorant in cheese, to detect the volume of pieces of red (or other colours) fruit in cartons of yoghurt, in a production line, to quantify the body composition, by a combined analysis of the distribution of water and fats, to quantify the quality of a mixture, and to detect a pollutant in mist.

Contrary to the case of a limpid medium containing a single colorant, the sole knowledge of the geometry of the injection/collection points of the light, associated to the knowledge of the initial intensity, are not enough. Other data is required.

In the case of limpid media, the analysis of the spectrophotometric properties permits the concentration to be determined using the Beer Lambert law.

The known spectrophotometry devices are all based on this analysis.

In the case of several colorants whose mixture is unknown, or in the case of several colorants of which one is unknown, several chemometric methods permit certain classes of these inverse problems to be resolved.

The spectral chemometric methods may be applied to many fields, in particular biology.

This invention proposes spectral and temporal chemometry in pulsed and differential modes.

In the invention, we take account of the objects that are diffusing or turbid and/or a complexity which prevents the analysis by classic optical geometry (Beer Lambert law).

In these cases, the light journeys can no longer be assimilated to an estimated distribution by a Dirac distribution. The journeys of the electromagnetic wave form a more or less complex distribution which is most often an unknown.

On this subject, three types of problems are considered:

1) vision in troubled media.

In fact, all diffusing media are polyphasic systems with dimensions close to the wavelength of the light used to light up the medium.

On this subject, let us consider an example of six media with 2 phases. This example is schematically illustrated by FIG. 4, where the two phases are respectively composed by a matrix I and an element II.

The size of the element is noted II.

In FIG. 4, we have considered these six elements noted A to F:

A: element that is more transparent and of the same absorption as the matrix,

B: element that is more transparent and with stronger absorption than the matrix, C: element that is diffusive like the matrix and with stronger absorption than the matrix, D: element that is more diffusive than the matrix and of the same absorption as the matrix, E: element that is more diffusive than the matrix and with lower absorption than the matrix, F: element that is more diffusive than the matrix and with higher absorption than the matrix.

In addition, the various cases of the frontiers of these volumes needs to be dealt with (conditions at absorbent or reflective limits, of a third type or unknown), either between the matrix and the outside or between the matrix and the sub-volume concerned.

If the medium cannot be homogenised, (D much greater than the wavelength and/or periodicity and/or period of the volume concerned of too little interest), then the aim is to carry out a tomography, in particular to identify one or more of the sub-volumes whose optical properties are very different from those of the matrix. The use of spectro-temporal imaging and its partial derivatives thus require displacements between the point of impact of the measurement laser beam and the detection permitting the use of the space type partial derivatives.

2) Spectroscopy in troubled media.

Spectro-temporal imaging permits the problems of chemometry to be resolved for non transparent media that may be homogenised, in the mathematical sense. For the homogenisation theory in particular in media that may be modelled by two means periodically, we recommend consulting the following book:

N. Bakhvalov and G. Panasenko, "Homogenisation: averaging processes in periodic media" 1989.

These problems of polyphasic media are revealed to concern the majority of measurement cases on real objects in chemistry, in biology as well as in many sectors of industry (powders, aerosols, suspensions, for example).

In this case (2), the study medium may be brought to a periodic unit or one that comprises a large number of cells (or representative elementary volumes) of the type of the six examples A to f in FIG. 4.

The modelling of the geometry and the optical phenomena are one of the key factors in resolving the problems to be dealt with. We have only considered here the simple models, called single scale, but the various systems of diffusion/diffraction/induction each require an adapted scale.

3) two types of distributions.

The measurement leads to a spectro-temporal image which describes two types of distributions:

a distribution in derivable time, a distribution in derivable wavelength.

The unit is a whole number of single photo-electrons or an arbitrary unit (lit pixels).

For turbid media (absorbent or highly diffusing), the analysis of these distributions in time often rests on the estimation of the diffusion.

The classes of spectral distribution depend above all on the absorption spectra of the colorants. Calculation programmes in quantum chemistry permit fairly simple absorption molecule spectra to be obtained. Otherwise, the ultraviolet close to infrared spectra data bases may be used.

On this subject, refer to:

H. Du et al. "PhotoChemCAD: a computer aided design and research tool in photochemistry", Photochemistry and Photobiology, 68, 141-142, (1998).

The problems where the spectral distribution is not monotone presence of an absorption peak or trough or a transmission peak or trough in the spectral window tested) form the class which is the easiest to process with partial derivatives of the order of one and two.

Contrary to the case of a limpid medium, containing one or more well mixed colorants, the problems that we wish to resolve require, in addition to the spectral distribution, the temporal distribution of the optical pulse and its derivatives.

One aspect of the invention is the search for integration windows (spectral and temporal distributions) permitting the signal to noise ratio to be improved and to involve the dynamics between the counting of diffusive photons and ergodic photons.

In the prior art, the differential spectrophotometry aspects were covered with respect to the spectral distribution without pulse mode. Similarly, studies on temporal distributions with discrete wavelengths have been carried out.

The conjunction of the contributions of the differential spectrometry and the analysis of the migration of the photons constitutes an important aspect of the invention.

We will provide hereunder an example of the device in compliance with the invention, permitting the spectro-temporal image to be obtained.

As concerns the pulse source, at least two technical choices are possible:

a) a source of femtosecond pulses ultra-short in themselves (ultra-short oscillator), and b) means for generating a femtosecond or picosecond continuum and/or parametric amplification of a mono-filament continuum.

The detector is a streak camera. At least two operating modes are possible:

i) the synchronous scanning mode or synchro-scan mode ii) the single shot mode.

FIG. 5 schematically illustrates an example corresponding to the case b) –1).

The device of FIG. 5 successively comprises:

a femtosecond laser.

means 10 for formatting the light supplied by this laser 8, this formatting being for example a single lens, the light thus formatted then reaching a volume 11 of the non-limpid medium designed to create a femtosecond continuum subsequently authorising the derivations according to the wavelength.

means 12 for filtering the light issued from the volume 11, means 14 for guiding this filtered light, for example an optical fibre, a polychromater, 16, which receives this guided light, subsequently authorising the derivations according to the wavelength, a streak camera 18 which captures the light emitted from the polychromater 16 and operates in synchronous scan mode, subsequently authorising the derivations according to the wavelength and flying time, electronic and computer means 20 for processing the electrical signals supplied by the camera 18, these electronic and computer means 20 being designed to carry out the binarisation and counting of the single photo-electrons and to provide the final image and its partial derivatives with respect to the flying time and the wavelength, and means 22 for displaying the results obtained thanks to the electronic and computer processing means 20.

The flying time is defined as the time for the propagation of the light pulse between the entry point in the volume 11 studied and the exit point in the streak camera 18.

The device of FIG. 5 provides an image on, for example, 640×480 pixels, and the image of which is derivable in wavelength and flying time. By way of example, each pixel is coded on 8 bits and then stored on 16 or 32 bits. This whole number represents the number of single photoelectrons or pixels lit that are counted during a certain measuring time called the integration time.

The analogue mode may also be used but the counting mode in streak camera mode is more advantageous, especially due to the fact that it is more dynamic and the high signal/noise ratio that it permits to obtain.

It should be noted that the spectro-temporal fluorescence imaging known in the state of the technique, for example of the same type as that developed by the Hamamatsu company, provides access to spectral and temporal distributions that are specific to the analysis of the multi-component fluorescence decline time.

The spectro-temporal transmission imaging, which is used in this invention, provides access itself, to spectral and temporal distributions and to their partial derivatives that are specific to the analysis of the propagation/absorption modes in non-limpid media.

The problem of the study of widening by increasing the diffusion of the pulse transmitted and the widening by reduction of the absorption of the pulse transmitted and in particular of the descending edge is also of a statistical nature.

To resolve the two classes of problems that are raised (homogenisation—sense of the mean of a concentration test, calculation of the mean concentration and its fluctuations), all of the raw information available is used and especially all of the partial derivatives.

For a mean distance between the point of impact p (FIG. 5) of the light emitted by the laser 8 and the detector, which is to say the camera 18, this raw information consists of a spectro-temporal transmission image that may be derived.

Contrary to a topographic image, we therefore have a grandeur that is very different for each dimension, which is to say the wavelengths (in nm) and a deflection time (in ps).

The distributions are therefore very different.

Contrary to a spectro-temporal fluorescence image, whose purpose is to determine the fluorescence decline time of the various fluorophores (S. MOTTIN, C. TRAN-MINH, P. LAPORTE R. CESPUGLIO and M. JOUVET Fiber optic time resolved fluorescence sensor for in vitro cerotonin determination, Applied Spectroscopy, 1993, 47, 590-597), the spectro-temporal transmission imaging has more complex distributions.

Purely by way of information and in no way restrictively, the laser 8 used has the following characteristics:

Oscillator Ti: Sa 800 nm 78 MHz 500 mW; chirp pulse amplification chain, Ti:Sa pumped by a 10 W YLF, permitting 0.7 W, 1 KHz, 150 fc at 800 nm to be obtained; generation of continuum.

With these characteristics, the rate is 1000 pulses per second.

A streak camera 18 may be used for which the time of each image is an integration on 33 ms, which corresponds to 33 laser shots.

However, a single shot mode and single hit mode remain accessible.

Two final processing modes are possible for the counting:

1) thresholding and binarisation (1 photoelectron on average lights less than 5 pixels), the unit in this case being the count, and 2) thresholding and then binarisation and a morphological analysis aimed at reducing the number $N_p$ of these lit pixels to 1 central pixel lit, the unit then being truly the single photoelectron.

This second mode requires suitable counting.

These two modes exist in derivable spectro-temporal transmission imaging.

For each image (corresponding to an integration over 33 ms), the counting rate can be approximately calculated:

If the distribution is uniform and if a limit is set at 1% of the counting ratio to prevent two photo-electrons from falling on the same group of pixels and being counted as a single photo-electron, then a coarse value is obtained which is of the order of 307200×0.01=3000 single photo-electrons per image.

If the distribution is of the "exponential×Heaviside function" type and if a final dynamic of 1000 is desired, with a counting ratio [1000-1] over 415 pixels/480 pixels, you then have, over a total deflexion of 1100 ps, a distribution De (t) which is uniform over the 640 pixels and such that, for all wavelengths:

$$De(t)=1000 \times \exp(-t/tm) \text{ with } tm=1100/8=137ps.$$

If a limit is set at a counting ratio of 1% for the final counting zone [1000-300], then we have 72 pixels×640=46080 pixels and 46080×0.01=460 single photo-electrons per image.

If the spectral distribution $D_\lambda(x)$ is not uniform but Gaussian and centred on the $320^{th}$ pixel and if it is wide enough to have a dynamic of 1000 over 52 pixels, then the following can be written $D_\lambda(x)=\exp(-((x-320)/100)^2)$ where x is the pixel number.

A distribution for absorption of the Lorentz type or a non-symmetrical distribution like the Lowry and Hudson distribution could also be used.

On this subject reference may be made to the following document:

C. Sandorfy, "Les spectres électroniques en chimie théorique (Electronic spectra in theoretical chemistry), Paris, Revue d'optique théorique et instrumentale, 1959.

Likewise, 72 pixels×220 pixels×0.01=158 single photo-electrons per image are obtained.

With these two distributions, the secure count is very roughly of the order of 160 single photo-electrons per image. With 30 images per second, we get to about 5000 SPE per second and on average 5 SPE per laser shot at the rate of 1 KHz.

Compared with spectro-temporal fluorescence imaging, this brief illustrative calculation demonstrates that spectro-temporal transmission imaging presents a considerably more secure count.

It is specified that two approaches are possible in the present invention, namely an empirical approach and a Beer-Lambert spectrophotometry generalisation.

In the first approach, the target is detection only and in the second approach the target is measurement.

The derivable spectro-temporal images and their derivatives can be connected to a semiological, non-optical criterion, of a statistical nature, for example the ripening of a fruit, the quality of a UHT process for milk, the mechanical properties of a diffusing plastic, the quality of a ceramic dispersion.

Purely by way of illustration and in no way restrictively, the invention has been implemented for various objects such as potatoes, eggs and apples. In each case, a stack of derivable images has been obtained:

a first image constituted by a set of points in a Number of SPE frame (in an interval of wavelengths, for example 700 nm-725 nm) as a function of Time (ps) and macroscopic Time (s), a second image constituted by a set of points in a Number of SPE frame as a function of Wavelength (in nm), and macroscopic Time (s), a third so-called basic image, constituted by a set of points (number of SPE) in a Wavelength (in nm)–Time (in ps) frame.

Let us now consider the Beer-Lambert spectrometry generalisation.

Generally speaking, it is necessary to establish a mathematical model of the structure of the medium to be tested. The most straightforward case consists in considering the object to be measured as a model in homogeneous isotropic suspension. In this case, numerous mathematical models (apart from methods of the Monte Carlo type) have already been proposed and are based especially on the approximation of the diffusion and, more generally, on the theory of radiative transfer.

It is specified that, in case of two of non-miscible phases, diffusion becomes non-linear when the volumic fraction exceeds a few in a thousand.

In the linear case of very weak diffusion, an equivalent of the Beer-Lambert law can be used, since turbidity is then considered as pseudo-absorbance:

Log $(I/I_o) = -L/L^*$ where $L^*$ is the length of diffusion.

When this threshold is exceeded, the multiple diffusion system commences.

For a dilution of 2% or less than 2%, simple diffusion applies.

Particle size distribution analysis methods often use a dilution process to return to the linear situation of simple diffusion where the theory of Mie remains applicable.

In the present invention, it is proposed to process high load and coloured suspensions, which authorise measurements in situ, without contact and without dilution. In this case, the Beer-Lambert spectrometry generalisation applies in relation to absorbers with the imaging techniques proposed.

With the pulse spectrophotometry technique, the case has for example been studied of various concentrations of a colorant in semi-skimmed UHT milk. The non-use of partial derivatives has emphasized the difficulty of a reliable measurement.

A device was used that is identical to that used in conventional spectrophotometry (10 mm trough, detection and collection centred on one surface). A sequential procedure was used but a double beam method would be easy to implement.

The spectro-temporal image with its partial derivatives of the continuum in the air then that of the undiluted semi-skimmed UHT milk with no added colorant were also recorded. Then small quantities of colorant previously diluted in water were added. The detection of 50 nanomoles/l of this colorant was obtained.

It should be noted that in conventional spectrophotometry the spectrum of a colorant is always recorded relative to a reference body which is generally pure solvent. Milk may be considered here as the reference solvent. The spectral range is selected relative to the peak of this colorant but can be easily transposable in ultraviolet or the near infrared.

It was found that semi-skimmed UHT milk diffuses a lot and absorbs in the blue-green range. Comparison with water shows a considerable degree of absorption in the blue-green range, which is partly related to the free flavins.

The invention allows the mean of the concentration of these endogenous colorants to be thus measured over a volume of a few $cm^3$ in the example proposed. But more appreciable volumes (a few $dm^3$) can be tested with a fairly powerful source or a fairly long measuring time.

Access to a volumic mean of this type of control in situ is likely to constitute a good milk quality index.

The pulse and differential spectrophotometry used in the invention allows a concentration of absorber to be measured in a non-limpid medium. It also allows concentrations of diffusers to be measured. Additionally, it allows the quality of the direction of the mean of these concentrations to be quantified (formation of a mean or non-homogenisation).

It should additionally be noted that the invention allows derivable spectro-temporal imaging to be implemented with a single white light laser pulse, which is impossible with a tunable scanning system.

Additionallly, the invention has the advantage of being a contactless technique, allowing global measurement in situ and on line. For example, pots of yoghurt or diffusing objects can be measured on line in their own container.

The invention additionally allows information to be acquired about the volume of each object (and about absorbent sub-volumes, for example pieces of fruit), about the quality of the fermentation and about the visual quality.

Moreover, the invention constitutes a rapid and reliable technique in the case of an empirical approach.

In fact, it applies generally to the measurement of diffusing objects.

In the case of exact measurements of concentrations of absorbers (and/or diffusers), the invention can be considered as a Beer-Lambert spectrophotometry generalisation of non-limpid media, but without scanning and in pulse mode, the spectrophotometry of the invention being additionally differential.

Moreover, for the implementation of the invention, the impact-detection length should be adapted as a function of the degree of diffusion and absorption.

However, this adaptation is not necessary if the light source or the collector is subjected to displacements.

Hereinafter are shown the advantages of the partial derivatives of the spectro-temporal image that is used in the invention.

Publications about radiative transport in optics are very numerous [Ishimaru, 1978; Ishimaru A., "Wave propagation and scattering in random media" New York, 1978.], [Mottin, 2001; Mottin S. and Laporte P., Systèmes femtosecondes pour l'étude des milieux hétérogènes compartimentés absorbants et diffusants dans "systémes femtosecondes" Ed. P. Laporte, F. Salin and S. Mottin, Puse, pp. 295-310, 2001]. According to the well-known approximation of diffusion, the interactions can be reduced to the following equation:

$$\left[\frac{\partial}{\partial t} - (D)\nabla^2 + \left(\frac{1}{\Sigma_a}\right)\right](u(r,t)) = S_0(r,t)$$

u (r, t) is the photon density (number of photons/$mm^3$ or in J/$mm^3$).

The tested medium is reduced to two quantities

<$1/\Sigma_a$>=<$c\mu_a$>. This quantity is consistent with first order kinetics (in $ps^{-1}$). $\Sigma_a$ is consistent with a time. c is the universal constant of the speed of light in the void (0.3 mm/ps), divided by the mean index of the medium (n=1.4). And $\mu_a$ is the coefficient of absorption in mm$^{-1}$.

<u>D</u> is the coefficient of optical diffusivity in mm$^2$/ps with <u>D</u>=cD. D=$(3(\mu a+\mu_a'))^{-1}$. $\mu_a'$ is the reduced coefficient of diffusion in mm$^{-1}$.

This approximation of diffusion is only usable if you are far away from short times (in other words if t is much greater than $(cD^{-1})^{-1}$ and if $<\mu_a>$ is much lower than $<\mu_a'>$.

For a simple case (semi-infinite medium, constant homogenisable $<\mu_a>$ and $<\mu_a'>$, a source point considered as a Dirac spatial distribution, a collection point considered as a Dirac spatial distribution, and p the distance between these two points), the Patterson team [Kienle, 1997; Kienle A., Patterson M. S., Improved solutions of the steady state and the time-resolved diffusion equations for reflectance from a semi-infinite turbid medium, J. Opt. Soc. Am. A 14 246-254, 1997] has published the analytical solution. t=0 is the moment of injection in the volume from the source point:

$$R(\rho, t) = U(t)\frac{1}{2}(4 \times \underline{D})^{-3/2, -5/2}\exp\left(-\frac{1}{\Sigma_a}\right)$$
$$\exp\left(-\frac{t_F(\rho, \underline{D})}{t}\right)\left\{z_0\exp\left(-\frac{t_F(r_1, \underline{D})}{t}\right) + z_{-1}\exp\left(-\frac{t_F(r_{-1}, \underline{D})}{t}\right)\right\}$$

with $r_1=z_0$, $z_0=(\mu_a')^{-1}$, $r_{-1}=z_0+2z_b$, $z_b$=2D (1+Ra/1−Ra) and $R_d$=1.440n$^{-2}$+0.710n$^{-1}$+0.668+0.636n, n being the index of refraction which depends on the wavelength. U(t) is the Heaviside function. The Fourier time is denoted $t_F$ ($\rho$, <u>D</u>)=$\rho^2/(4<\underline{D}>)$.

For a given $\rho$, R($\rho$,t) is a function of the flying time and the wavelength.

It can also be approximated by ignoring the role of the limit conditions by:

$$rr[t, \lambda] := \beta z[\lambda]\frac{e^{-(t/Ta[\lambda]+TF[\lambda]/a)}}{t^{5/2}}$$

with β constant relative to t and λ,$T_a(\lambda)=\Sigma_a$, $T_F(\lambda)$, both of them functions of the wavelength λ (which are the two functions sought).

This analytical solution is an approximation of the probability distribution of the spectro-temporal image. With the counting mode, adding a Poisson type adjustment to this analytical solution is possible.

One of the main innovative features of the present invention is the use of the partial derivatives according to wavelength and time of this image.

For cases of static spectrometry the use of the derivative (in these cases, non partial) is well known particularly in respect of chemometrics in limpid media. In the present invention, in the context of pulse spectrometry (femto, pico or nanosecond) the joint use of the partial derivatives according to wavelength and flying time is necessary for non-limpid media.

A) The advantage of the nth derivations as a function of the flying time appears clearly below (only the first and second derivatives are specified):

1) The ratio of the partial derivative as a function of flying time by the function itself is equal to:

$$\frac{\frac{\partial}{\partial t}(\text{image})}{\text{image}} = -\frac{1}{Ta[\lambda]} - \frac{5}{2t} + \frac{TF[\lambda]}{T^2}$$

2) The ratio of the second partial derivative as a function of the flying time by the function is equal to:

$$\frac{1}{Ta[\lambda]^2} + \frac{5t - 2TF[\lambda]}{Ta[\lambda]t^2} + \frac{35t^2 - 28TF[\lambda] + 4TF[\lambda]^2}{4t^4}$$

and so on for the nth derivatives.

Briefly it may be observed that a) the function in $t^{-5/2}e^{-(t/TA+TF/t)}$ has disappeared b) the line following λ of the reduced maxima coincides with the solution of a simple equation of the second degree the only realistic solution of which is:

$$t_{\max}[\lambda] = \frac{5}{4}Ta[\lambda]\left(\sqrt{1 + \frac{16TF[\lambda]}{25Ta[\lambda]}} - 1\right)$$

c) the lines following λ of the reduced inflexion points correspond to the solutions of an equation of the fourth degree:

This equation still has 4 solutions two of which are real and positive. These last two realistic solutions correspond to the 2 inflection points for a single given wavelength.

B) For partial derivatives as a function of the wavelength, the problem is trickier since the functions Ta[λ], TF[λ] and Z[λ] are not initially known.

1) Nonetheless Z[λ] and TF[λ] are often monotone since $\mu_a'[\lambda]$ is very often so (with Z[λ]=1/$\mu_s'$[λ] and TF [λ]=3/$4\rho^2\mu_s'[\lambda]/c[\lambda]$) therefore their partial derivatives as a function of λ are of the same sign on the spectral window.

2) Conversely 1/Ta[λ] (equal to $\mu_a[\lambda]c[\lambda]$) presents all the scenarios of continuous functions with maxima and minima. For the function μa[λ] which corresponds to the linear optical density of the spectrometry of absorption of limpid media, an abundant literature has already dealt with the advantage of the nth derivations (non partial derivations) and the dedicated methods of analysis. These approaches are limited to a spectral vector with one dimension and never extended to a spectro-temporal image with two dimensions with a flying time as a second coordinate. One of the innovative activities, here clearly and analytically specified, broadens these methods to the partial derivatives in the case of spectro-temporal absorption imaging of non-limpid media.

C) Moreover, an example of the use of a crossed partial derivative is the derivation following λ consecutive to the derivation following the flying time. This derivative is cancelled for the lines of reduced maxima.

$$\frac{\partial}{\partial \lambda}\left(\frac{\frac{\partial}{\partial t}(\text{image})}{\text{image}}\right) = 0$$

A very straightforward formula is obtained:

$$\frac{\partial(\mu_d[\lambda]c[\lambda])}{\partial\lambda} = \frac{3}{4}r^2 r^{-2} \frac{\partial}{\partial\lambda}\left(\frac{\mu'_s[\lambda]}{c[\lambda]}\right)$$

If we ignore the variations in the average speed of propagation as a function of λ then c[λ]=c.

Thus for the lines of reduced maxima the size of the a dimensional quantity $\Omega=3/4\rho^2/(ct)^2$ is clear:

$$\frac{\frac{\partial(\mu a[\lambda])}{\partial\lambda}}{\frac{\partial(\mu'_s[\lambda])}{\partial\lambda}} = \Omega$$

In all these methods, the spectro-temporal image is considered only as a zero order moment where all the authors manipulate it (for example moving to the Log(image)) only in itself without partial derivation operators. It is the partial derivatives which best reveal the nature of this imaging.

So we have just seen a method example using the relationships between the partial derivatives and the image itself. Finally the data sought, the function $\mu_a[\lambda]$, or a few exceptional points (maxima, minima, maximum slope zone, inflection points etc.) of a non-limpid medium can be extracted through the processes proposed in the present invention. If the study of the medium is more physical (search for $\mu_a[\lambda]$ and exceptional points) then the approaches are also of the same order. If the purpose is the complete study of the non-limpid medium then the processes of differential spectro-temporal imaging also allow $\mu_a[\lambda]$ and $\mu_a'[\lambda]$ and the exceptional points to be qualified and quantified.

We have therefore just shown, in an appropriate mathematical language, the advantages of the partial derivatives of the spectro-temporal image.

It should be noted that to implement the present invention, one or more monochromatic light pulses can be used, in order to illuminate the non-limpid medium, and acquire at least one spectro-temporal transmission image from this medium, by carrying out a spectral scan.

But one or more large spectrum light pulses can also be used, to illuminate the non-limpid medium, and acquire at least one spectro-temporal transmission image from this medium, without spectral scanning.

By "wide spectrum light pulse" is understood a light pulse the spectrum of which is greater than or equal to the spectral window of the acquisition means, namely the polychromator and the streak camera in an example given above.

The invention claimed is:

1. Differential spectrophotometry process, for analysing a non-limpid medium (11), this process being characterised that:
   the non-limpid medium is lit by at least one light pulse allowing the subsequent use of the partial derivative, as a function of the wavelength, of at least one spectro-temporal transmission image acquired from the medium thus lit,
   at least one spectro-temporal transmission image, in counting mode is acquired, through at least one light collector, from the medium thus lit, allowing the subsequent use of the partial derivatives of the image as a function of the wavelength and of the flying time of the light pulse, and
   the image and its partial derivatives are processed as a function of the wavelength and of the flying time so as to acquire information about the non-limpid medium.

2. Process according to claim 1, wherein use is made, for the purpose of qualifying the degree of homogenisation of the tested medium (11) or of detecting a singularity of absorption and/or diffusion, of the partial derivatives related to variations in flying time and in spectrum of the diffusive and ergodic photons not absorbed over a wide spectral range by the medium, these diffusive and ergodic photons being emitted by the medium while it is lit.

3. Process according to claim 1, wherein use is made conjointly of the partial derivatives related to the flying time of the light pulse and to the spectral data so as to establish a spectro-temporal identity card of the non-limpid medium (11).

4. Process according to claim 1, wherein the collector is lit without probing the medium (11) and at the same time the non-limpid medium is lit by one or more light pulses authorising derivable spectro-temporal imaging relative to the wavelength and to the time, with two peaks simulating a double beam.

5. Differential spectrophotometry device, for analysing a non-limpid medium (11), this device being characterised in that it includes:
   a pulse light source (8) to light the non-limpid medium and which allows the subsequent use of the partial derivative, as a function of the wavelength, of a spectral and temporal transmission image acquired from the medium thus lit,
   means (18) for acquiring, from the medium thus lit, a spectral and temporal transmission image, in counting mode, allowing the subsequent use of the partial derivatives of the image as a function of the wavelength and of the flying time of the light pulse, and
   means (20) for processing this image, considered as the zero order moment, and its partial derivatives as a function of the wavelength and of the time, in order to acquire information about this medium.

6. Device according to claim 5, wherein the pulse light source (8) includes means for the non-linear generation of femtosecond or picosecond light pulses allowing the use of the partial derivative as a function of the wavelength.

7. Device according to claim 5, wherein the pulse light source includes means (8) for generating and amplifying the femtosecond or picosecond or nanosecond continuum of a continuum, the continuum directly allowing the use of the partial derivative as a function of the wavelength.

8. Device according to claim 5, wherein the acquisition means (18) include a streak camera in counting mode.

9. Device according to claim 5, wherein the acquisition means include a streak camera (18) for single photoelectron counting in single stroke operational mode or in synchro-scan operational mode or in analogue mode.

10. Differential spectrophotometry process according to claim 1, allowing the establishment of a genuine optical identity card of the volume tested, in other words a faithful signature of the statistical nature of the medium (11) relative to the more a less homogeneous contents of the diffusers and absorbers, this optical identity card being in the form of one or more spectro-temporal images that allow simultaneous access to the temporal distributions for a given spectral window, to the spectral distributions for a given interval of time, to the partial derivatives of these two distributions and to their integrals.

11. Spectrophotometry and tomography process according to claim 1, wherein use is made conjointly of the partial derivatives, with respect to wavelength, flying time and space, of the spectro-temporal images and mono-point modes with spatial scanning or commuted multi-point modes of the injection zones and/or light collection zones, the use of the space type partial derivatives then being possible and allowing certain cases of non-constant density in the volume tested to be processed, this tomography process with spectro-temporal image differentials allowing, on the one hand, an identification of a singularity of the concentration of absorbers and/or diffusers, on the other hand, a molecular identification of these absorbers, the injections and collections of light being able to be implemented either on the surface or within the volume.

12. Differential spectrophotometry process according to claim 1, wherein use is made conjointly of the partial derivatives, relative to the wavelength and the time, of spectro-temporal transmittance imaging and the counting mode by binarisation of the image then detection of a pixel zone attributable to a photoelectron and reduction of this zone to a single lit pixel, or to a sub-pixel scale, in order to increase the dynamics and qualify the single photo-electron measurement.

13. Spectrophotometry process according to claim 1, wherein use is made, for the purpose of measuring very slight variations of an absorber, of the partial derivatives in time and wavelength of the temporal queue related to the ergodic photons diffused by the medium (11) while it is lit.

14. Differential spectrophotometry process according to claim 1, wherein use is made, for the purpose of measuring or homogenising contents of absorbers and/or diffusers, of spectro-temporal imaging and the operators $\partial/\partial t$, $\partial^2/\partial t^2$, $\partial/\partial\lambda$, $\partial^2/\partial\lambda^2$, $\partial^2/\partial t\partial\lambda$ up to higher orders, these operators applying to the spectro-temporal image.

15. Differential spectrophotometry process according to claim 1, wherein use is made conjointly of fluctuations of the spectro-temporal transmittance images and the associated operators so as to carry out dynamic opacimetry, colorimetry and particle size distribution measurements.

* * * * *

UNITED STATES PATENT AND TRADEMARK OFFICE
CERTIFICATE OF CORRECTION

| | | |
|---|---|---|
| PATENT NO. | : 7,265,826 B2 | Page 1 of 1 |
| APPLICATION NO. | : 10/522726 | |
| DATED | : September 4, 2007 | |
| INVENTOR(S) | : Mottin | |

It is certified that error appears in the above-identified patent and that said Letters Patent is hereby corrected as shown below:

On the title page, Item (30), the Foreign Application Priority Data has been omitted. Item (30) should read:

-- (30) Foreign Application Priority Data

Jul. 31, 2002   (FR) ...................................................... 02-09755 --

Signed and Sealed this

Sixth Day of November, 2007

JON W. DUDAS
*Director of the United States Patent and Trademark Office*